(12) United States Patent
Holtkamp

(10) Patent No.: US 11,357,717 B2
(45) Date of Patent: Jun. 14, 2022

(54) PRODUCTION, COMPOSITION AND APPLICATION OF PREPARATIONS IN A TWO-CHAMBER APPLICATION DEVICE FOR NEUTRALIZING AND INACTIVATING OXIDIZING, CAUSTIC AND IRRITATING CHEMICALS ON THE SKIN

(71) Applicant: Field Forensics, Inc., St. Petersburg, FL (US)

(72) Inventor: Katharina Holtkamp, Cloppenburg (DE)

(73) Assignee: Field Forensics, Inc., St. Petersburg, FL (US)

( * ) Notice: Subject to any disclaimer, the term of this patent is extended or adjusted under 35 U.S.C. 154(b) by 221 days.

(21) Appl. No.: 16/719,595

(22) Filed: Dec. 18, 2019

(65) Prior Publication Data
US 2020/0289395 A1     Sep. 17, 2020

(30) Foreign Application Priority Data
Oct. 27, 2018   (DE) .................... 10 2018 008 512.1

(51) Int. Cl.
| | | |
|---|---|---|
| *A61K 8/67* | (2006.01) | |
| *A61K 8/20* | (2006.01) | |
| *A61K 8/34* | (2006.01) | |
| *A61K 8/368* | (2006.01) | |
| *A61K 8/44* | (2006.01) | |
| *A61K 8/86* | (2006.01) | |
| *A61Q 19/00* | (2006.01) | |
| *B05B 7/04* | (2006.01) | |

(52) U.S. Cl.
CPC ............... *A61K 8/676* (2013.01); *A61K 8/20* (2013.01); *A61K 8/345* (2013.01); *A61K 8/368* (2013.01); *A61K 8/44* (2013.01); *A61K 8/86* (2013.01); *A61Q 19/00* (2013.01); *B05B 7/0408* (2013.01); *A61K 2800/882* (2013.01)

(58) Field of Classification Search
CPC ............................... A61K 31/19; A61K 31/34
USPC .......................................................... 514/474
IPC .......................................................... A61Q 19/00
See application file for complete search history.

(56) References Cited

U.S. PATENT DOCUMENTS

| | | | |
|---|---|---|---|
| 2,249,903 | A | 7/1941 | Lautenschlager et al. |
| 4,837,019 | A | 6/1989 | Georgalas et al. |
| 5,140,043 | A | 8/1992 | Darr et al. |
| 5,958,436 | A | 9/1999 | Hahn et al. |

FOREIGN PATENT DOCUMENTS

| | | |
|---|---|---|
| EP | 1265595 B1 | 6/2005 |
| WO | 2005117852 A1 | 12/2005 |

*Primary Examiner* — Walter E Webb
(74) *Attorney, Agent, or Firm* — Christopher Paradies; Paradies Law P.A.

(57) ABSTRACT

A device and protective composition is described that is used in the context of first aid for skin contact with acids, bases, oxidizing agents, formaldehyde and fluorides serving to neutralize and inactivate the chemicals. The device comprises a two-chamber applicator that contains a first preparation in a first chamber, such as an antioxidant, and a second preparation in a second chamber, such as a solution that contains a buffer and a calcium salt. The two preparations are mixed just before application and are applied to the affected areas by the device.

12 Claims, No Drawings

PRODUCTION, COMPOSITION AND APPLICATION OF PREPARATIONS IN A TWO-CHAMBER APPLICATION DEVICE FOR NEUTRALIZING AND INACTIVATING OXIDIZING, CAUSTIC AND IRRITATING CHEMICALS ON THE SKIN

CROSS RELATED APPLICATIONS

This application claims priority to German application no. 10 2018 008 512.1

FIELD OF THE INVENTION

The field relates to devices and methods of neutralizing or inactivating a variety of hazardous substances.

BACKGROUND

Strong oxidizing agents such as chlorine gas, chloramines, hypochlorites, chlorine dioxide, bromine, iodine, Hydrogen peroxide, other peroxides and ozone serve as broad disinfectants in medicine, in personal hygiene, in the production of food and in Drinking water treatment. Strong oxidizing agents of various kinds (organic and inorganic) serve in the chemical industry and in other production facilities as Reagent for chemical reactions, especially in the textile and paper industry Bleaching and are ingredients in bleaching detergents and cleaning agents. Strong Oxidants can continue to be used as sabotage and chemical warfare agents (e.g. chlorine gas in the civil wars in Syria and Iraq, chlorine cyanide in World War I). Triacetone peroxide is formed from hydrogen peroxide and acetone and can be exploded by impact or ignition sources, even if it is in the form of a loose powder.

Strong acids such as hydrochloric acid, sulfuric acid, nitric acid, phosphoric acid, acetic acid and strong bases such as caustic soda or potassium hydroxide serve as cleaning agents or chemicals in the domestic area, in the production of food and in the treatment of drinking water. They continue to serve in the chemical industry and in other production facilities as reagents for chemical reactions. They can still be used as sabotage agents. Strong oxidizing agents are also sometimes strong acids (e.g. peracetic acid, Nitric acid).

Formaldehyde and formaldehyde-releasing compounds are in larger quantities at the Textile finishing, in polymer production, for surface and room disinfection and in chemical industry used. The germicidal properties of formaldehyde result presumably from an interaction between the electrophilic carbonyl atom Amino groups in cell proteins and nucleic acids. The same reaction could cause the irritant and cytotoxic effects. Formaldehyde can cause cell membranes, cytoplasm, damage core components or DNA. High concentrations of formaldehyde are therefore cytotoxic. They lead to degeneration and necrosis of the epithelial cell layers Mucous membrane. See BUNDESINSTITUT FÜR RISIKOBEWERTUNG; Toxikologische Bewertung von Formaldehyd, Stellungnahme des BfR Nr. 023/2006 vom 30 Mar. 2006.

Inorganic fluoride ions can be used as free acid (hydrofluoric acid), as salts (fluorides) or as Hydrofluoride or ammonium fluoride occur. Fluorides are mainly used as a flux in metallurgy, the synthesis of organic fluorochemicals and gas-tight Sealing of fuel tanks used; the plastic tanks, made out of plastics such as PA (Polyamide) vaporized with the dissolved fluoride. Fluoridation is the addition of Fluorides especially for table salt, drinking water, milk, tablets and toothpastes for prevention of dental caries. When these products are consumed, there are no problems with the user toxic fluoride concentrations. Likewise, when using covalently bound Fluorocarbon compounds (e.g. polymers such as Teflon) no toxic fluoride concentrations occur. Only dissolved or soluble fluoride is toxic, especially here Hydrofluoric acid. The poisonous effect (fluorosis) is based in part on the precipitation of calcium fluoride of calcium needed for metabolism, and partly from the effect as protoplasmic and cell toxicity, which inhibits certain enzyme systems and protein synthesis. It manifests itself in damage to the bones, teeth, lung function, skin and metabolic disorders.

When accidental contact of certain gases and liquids with the skin, skin irritation or damage may occur, and the substances may penetrate through the skin. The skin and respiratory organs may experience irritation and burns or transdermal or transpulmonary poisoning may occur. See KEZIC, Sanja; NIELSEN, Jesper Bo, "Absorption of chemicals through compromised skin," International archives of occupational and environmental health, 2009, 82. Jg., Nr. 6 S. 677-688. This danger exists especially with hydrofluoric acid, ionic fluorides and nitric acid. This damage can occur both through direct contact with the substances and indirectly through evaporation of substances. See BRUZE, Magnus; FREGERT, Sigfrid; GRUVBERGER, Birgitta; "Chemical skin burns," In: Handbook of occupational dermatology, Springer Berlin Heidelberg, 2000 S. 325-332. Furthermore, contact with the harmful substances can occur through contaminated clothing, commodities, equipment and contact with contaminated surfaces.

The damaging effects of the oxidizing agents may be prevented by chemical reducing agents such as ascorbate, sulfite, thiosulfate, sulfide or thiols (glutathione, acetylcysteine, Dimercaptosuccinic acid, dimercaptopropansulfonic acid, 2-mercaptoethanesulfonate sodium, Penicillamine). See DARR, D., et al., "Topical vitamin C protects porcine skin from ultraviolet radiation-induced damage," British Journal of Dermatology, 1992, 127. Jg., Nr. 3 S. 247-253. Strong oxidizing agents present in explosives can be inactivated by reducing agents, thus preventing the explosive effect.

The damaging effects of strong acids and alkalis may be prevented by physico-chemical neutralization with buffers or buffer mixtures. For example, see Bundesverband der Unfallkassen, Informationen für die Erste Hilfe bei Einwirken gefährlicher chemischer Stoffe, München, August 1999 S. 128, and also see Europäische Kommission, Entschließung des Rates und der im Rat vereinigten Vertreter der Regierungen der Mitgliedstaaten vom 3.12.1990 zur Verbesserung von Prävention und Behandlung akuter Vergiftungen beim Menschen (90/C 329/03), Anhang 3: Zur Orientierung dienendes Verzeichnis der Antidote, Amtsblatt der Europäischen Gemeinschaften (1990) Nr. C 329 pp. 16-23.

Calcium gluconate or other soluble calcium salts may serve as an antidote for fluoride poisoning. As a result, the fluorides are precipitated as insoluble calcium fluoride and can no longer are taken up by the cells (5). With hydrofluoric acid, possible damage of both acid and fluoride may be avoided by the simultaneous addition of a soluble calcium salt and a buffer mixture.

Aldehydes may form corresponding imines with primary amines or amides, which negates skin irritant or other toxic properties. Amino acids are particularly suitable as reaction partners.

For the different skin-damaging chemicals, paragraph numbers [0008] to [0011] describe known possibilities for neutralization or inactivation, or there exists products with the corresponding individual indication. For example, in U.S. Pat. Nos. 5,140,043, 2,249,903 and EP1265595B1 stable ascorbic acid solutions are described, and in U.S. Pat. No. 4,837,019 a topical preparation with an amino acid buffer are described. In U.S. Pat. No. 5,958,436 and EP1758570A1 in turn are topical preparations with calcium salts for treatment of skin irritation or hydrofluoric acid poisoning.

In laboratories and Industrial companies, there are sometimes cold water showers so that water-miscible chemicals may be rinsed or diluted. However, there are, so far, no products for widespread use in accidental contact for a wide variety of chemicals that are suitable for the neutralization or inactivation of acids as well as bases, oxidizing agents, fluorides and formaldehyde, combined. The reason for this is, in particular, described in paragraph [0008], which lists reducing agents with other required ingredients and the optimal pH of approximately 5-7, which don't have sufficient stability in aqueous solutions, such that fabrication of a suitably stable medicinal product or medical device has not been possible heretofore.

U.S. Pat. No. 5,152,461 discloses a spray bottle providing a first container, a second container, and a mixing chamber, wherein the spray mechanism draws a first liquid from the first container and a second liquid form the second container and mixes the first liquid with the second liquid at a selected ratio before spraying the mixture from the spray bottle.

SUMMARY

The task was to provide a product that was in accidental contact with skin-irritating or skin-damaging chemicals: a) neutralize or inactivate the chemicals on the skin and in the top layers of the skin as quickly as possible; b) eliminate skin irritation after the neutralization or inactivation reaction of the chemicals; c) can be used without special knowledge of the chemical; d) is suitable for direct application at any time; e) can be stored for several years at the location of the possible hazard without loss of effectiveness; and f) can be used to avoid contamination also for clothing, equipment, life-saving appliances and first responders.

In one example, a method of production and composition of two liquid preparations to be stored separately from each other in a device containing two separate containers until application of the mixture formed by mixing the two liquid preparations shortly before application comprises (a) preparing a reducing agent dissolved in a mixture of water and an organic water miscible solvent that is stored in a first container of the device; and (b) preparing a solution of a buffer and a calcium compound dissolved in water that is stored in a second container of the device. For example, the two liquid preparations may be mixed together shortly before application in a ratio of 2:1 to 1:2. More preferably, the two liquid preparations are mixed together shortly before application in a ratio of 1:1. For example, the two liquid preparations may be mixed in a spray bottle know in the art that comprises a first container, a second container, a mixing volume and a spray head, which draws liquid in a selected proportion from the first container and the second container into the mixing volume before spraying the mixture from the spray head.

In one example, the two liquid preparations are mixed and immediately applied to affected areas of skin. For example, the two liquid preparations are mixed to form a mixture in a mixing chamber of the device immediately before spraying the mixture of the two liquid preparations on the affected areas of the skin. For example, the step of (a) preparing a reducing agent may adjust pH to a range of pH from 3 to 4 by adding hydrochloric acid while stirring in the absence of light at a temperature in the range from 15 to 20° C. and under inert gas atmosphere. For example, the step of (b) preparing a solution of a buffer and a calcium compound dissolved in water may adjust the pH of the solution to a range of pH from 5 to 7 by adding sodium hydroxide solution or hydrochloric acid while stirring at a temperature from 15 and 20° C. and under an inert gas atmosphere. For example, the step (a) preparing a reducing agent may select a reducing agent or mixtures of reducing agents in a percentage selected from 3% to 10%, and the reducing agent or mixture of reducing agents may be selected from ascorbic acid, sodium ascorbate, potassium ascorbate, Calcium ascorbate, ascorbic acid ester with fatty acids, cysteine, N-acetyl cysteine, sodium thiosulfate, sodium sulfide, glutathione, acetylcysteine, dimercaptosuccinic acid, dimercaptopropanesulfonic acid, 2-mercaptoethanesulfonate sodium, penicillamine, sodium sulfite, potassium sulfite, or mixtures of any of these. For example, the organic water miscible solvent may consist of one or a mixture of glycerol, propylene glycol, polyethylene glycol, glucose, lactulose, sorbitol, erythritol or dimethylsulfoxide. For example, the buffer substance or mixtures of buffer substances may be selected in a proportion of between 3 and 15%, and the buffer substance or mixture of buffer substances may be selected from the group consisting of glycine, lysine, alanine, glutamic acid, di-sodium hydrogen phosphate, sodium citrate, and tris (hydroxymethyl) aminomethane. For example, the calcium compound may comprise a calcium compound in a proportion of between 0.5% and 3%, and the calcium compound may be selected from the group of calcium compounds consisting of calcium chloride, calcium ascorbate, calcium gluconate, calcium lactate, Calcium citrate, calcium acetate, calcium glutamate, and combinations of any of these.

In one method of applying a first aid product for neutralization and inactivation of oxidizing, corrosive and irritating chemicals on the skin, the method may comprise preparing preparation (a) comprising a reducing agent dissolved in a mixture of water and an organic water miscible solvent; preparing preparation (b) comprising a solution of a buffer and a calcium compound dissolved in water; storing preparation (a) in a first container; storing preparation (b) in a second container; fluidically coupling the first container and the second container; mixing an amount of preparation (a) from the first container and an amount of preparation (b) from the second container to form a mixture; and immediately spraying the mixture on an area of skin after the step of mixing, and thus, neutralizing or inactivating any one or a combination of the following chemicals: nitric acid 65%; sulfuric acid 95%; hydrofluoric acid 40%; hydrochloric acid, smoking 36%; Sodium hypochlorite solution 10% active chlorine; hydrogen peroxide 30%; Peracetic acid 24%; ammonia 25%; caustic soda 32%; Calcium hypochlorite 76% active chlorine; Lithium hypochlorite 26% active chlorine; Formaldehyde 35%; or triacetone peroxide.

DETAILED DESCRIPTION

According to one example of the invention, this object may be achieved by two different preparations in one two-chamber application device, which has the following features: a first preparation contains a reducing agent or mixtures of reducing agents formed in a proportion between 3 and 10% which are selected from the group consisting of ascorbic acid, sodium ascorbate, potassium ascorbate, calcium ascorbate, ascorbic acid esters with fatty acids, cysteine, N-acetyl-cysteine, sodium thiosulfate, sodium sulfide, glutathione, acetylcysteine, dimercaptosuccinic acid, dimercaptopropanesulfonic acid, 2-mercaptoethanesulfonate sodium, Penicillamine, sodium sulfite and potassium sulfite. This reducing agent is under inert gas atmosphere kept at a stable temperature between 15 and 20° C. dissolved in one mixture of deionized water in a percentage of up to 15% and otherwise water-miscible organic solvents or substances formed from the group of substances selected from glycerol, propylene glycol, polyethylene glycol (MW 200 to 10,000), glucose, lactulose, sorbitol, erythritol and dimethyl sulfoxide.

The preparation may be combined with hydrochloric acid to set a pH from 3 to 5. A second preparation may be formed containing a buffer substance or mixtures of buffer substances in a proportion between 3 and 15%, which are selected from the group consisting of glycine, lysine, Alanine, glutamic acid, disodium hydrogen phosphate, sodium citrate and tris (hydroxymethyl)-aminomethane, as well as formed of a calcium salt or mixtures of calcium salts in a percentage selected between 0.5% and 3%, which may be selected from the group consisting of calcium chloride, calcium ascorbate, calcium gluconate, calcium lactate, calcium citrate, calcium acetate and calcium glutamate. The buffer substances and calcium salts are submerged in water kept at a stable temperature between 15 and 20° C. and dissolved under a protective gas. The pH may be adjusted to a value from 5 to 7 by adding sodium hydroxide solution or hydrochloric acid.

The two preparations are stored in two separate containers and mixed shortly before use in a ratio of 2:1 to 1:2, more preferably in a ratio of 1:1. The application device is designed such that application of the mixture is enabled from a single device immediately following mixing of the two separated preparations. The application takes place by spraying or spreading with the help of a sponge or a brush, which is preferably part of the application device.

Embodiment: Preparation 1 (Portions Per 100 ml, Preparation Under Nitrogen Fumigation and at Maximum 20.0° C.)

Water 11 milliliters
PEG 200 add 70 grams and mix
Glycerin, anhydrous add 9.7 grams and mix
Tergitol TMN 10 0.1 milliliter
ascorbic acid add 9 grams and stir gently until everything has dissolved.

Preparation 2 (Portions Per 100 ml, Preparation Under Nitrogen Fumigation and at Maximum 20.0° C.)

Calcium chloride 2 H2O 3 grams
Benzoic acid 0.1 grams
Tergitol TMN 10 0.1 milliliters
Water add 82 milliliters and stir until everything has dissolved
Glycine add 15 grams and stir until everything is dissolved.
Fill separate chambers of a double-chamber spray bottle, drawing equal amounts from each chamber with the actuation of the spray lever into a mixing chamber. The mixture is then dispensed from the mixing chamber via the spray mechanism.

In one example, preparation 1 has a pH of 4.05 and a Redox voltage of −183 mV, preparation 2 has a pH of 5.22 and a Redox voltage of −10 mV. After mixing the two solutions in a 1:1 ratio, the pH value is at 4.3 and the redox voltage at 31 mV (later rising slightly to 50 mV). By released enthalpy of solution the temperature rises by approximately 5 degrees K. The mixture then contains about 0.25 mol/l ascorbic acid and 0.1 mol/l calcium ions (corresponding to a binding capacity for fluoride of 0.2 mol/l) and has a buffer capacity or formaldehyde imine formation capacity of 1 mol/l.

In this example, changes during mixing with chemicals were examined in terms of its neutralizing or inactivating effect on different chemicals in terms of miscibility, pH change, change in redox voltage and temperature and observable changes of the mixture.

For example, changes for the following chemicals were checked: nitric acid 65%; sulfuric acid 95%; hydrofluoric acid 40%; hydrochloric acid, smoking 36%; Sodium hypochlorite solution 10% active chlorine; hydrogen peroxide 30%; Peracetic acid 24%; ammonia 25%; caustic soda 32%; Calcium hypochlorite 76% active chlorine; Lithium hypochlorite 26% active chlorine; Formaldehyde 35%; and triacetone peroxide.

The result are summarized as follows: all chemicals examined were miscible; Fluoride is precipitated within a few minutes, and so does partial precipitation of sulfate; acids and bases are buffered immediately to a pH value of 3.5 to 4.5; oxidizing agents are immediately reduced to a redox voltage <50 mV; reaction energies are absorbed in a limited amount as chemical energy; skin and consumer goods are well wetted; triacetone peroxide can no longer explode due to impact or sources of ignition.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

What is claimed is:

1. A method of production and composition of two liquid preparations to be stored separately from each other in a device containing two separate containers until application of the mixture formed by mixing the two liquid preparations immediately before application of the two liquid preparations as a first aid product for neutralization and inactivation of oxidizing, corrosive and irritating chemicals on the skin, the method comprising:
   (a) preparing a reducing agent dissolved in a mixture of water and an organic water miscible solvent that is stored in a first container of the device; and
   (b) preparing a solution of a buffer and a calcium compound dissolved in water that is stored in a second container of the device.

2. The method of claim 1, wherein the two liquid preparations are mixed together before application in a ratio of 2:1 to 1:2.

3. The method of claim 1, wherein the two liquid preparations are mixed together before application in a ratio of 1:1.

4. The method of claim 1, wherein the two liquid preparations are mixed and immediately applied to affected areas of skin.

5. The method of claim 4, wherein the two liquid preparations are mixed to form a mixture in a mixing chamber of the device immediately before spraying the mixture of the two liquid preparations on the affected areas of the skin.

6. The method of claim 1, wherein the step of (a) preparing a reducing agent adjusts pH of the reducing agent preparation to a range of pH from 3 to 4 by adding hydrochloric acid while stirring in the absence of light at a temperature in the range from 15 to 20° centigrade and under inert gas atmosphere.

7. The method of claim 1, wherein the step of (b) preparing a solution of a buffer and a calcium compound dissolved in water comprises adjusting a pH of the solution to a range of pH from 5 to 7 by adding sodium hydroxide solution or hydrochloric acid while stirring at a temperature from 15 to 20° centigrade and under an inert gas atmosphere.

8. The method of claim 1, wherein step (a) preparing a reducing agent comprises selecting a reducing agent or mixtures of reducing agents in a percentage selected from 3% to 10%, and the reducing agent or mixture of reducing agents are selected from ascorbic acid, sodium ascorbate, potassium ascorbate, Calcium ascorbate, ascorbic acid ester with fatty acids, cysteine, N-acetyl cysteine, sodium thiosulfate, sodium sulfide, glutathione, acetylcysteine, dimercaptosuccinic acid, dimercaptopropanesulfonic acid, 2-mercaptoethanesulfonate sodium, penicillamine, sodium sulfite, potassium sulfite, or mixtures of any of these.

9. The method of claim 8, wherein the organic water miscible solvent consists of glycerol, propylene glycol, polyethylene glycol, glucose, lactulose, sorbitol, erythritol or dimethylsulfoxide.

10. The method of claim 1, wherein step (b) preparing a solution of a buffer and a calcium compound dissolved in water comprises a buffer substance or mixtures of buffer substances in a proportion of between 3 and 15%, and the buffer substance or mixture of buffer substances are selected from the group consisting of glycine, lysine, alanine, glutamic acid, di-sodium hydrogen phosphate, sodium citrate, and tris (hydroxymethyl) aminomethane.

11. The method of claim 10, wherein the calcium compound comprises a calcium compound in a proportion of between 0.5% and 3%, and the calcium compound is selected from the group of calcium compounds consisting of calcium chloride, calcium ascorbate, calcium gluconate, calcium lactate, Calcium citrate, calcium acetate, calcium glutamate, and combinations of any of these.

12. A method of applying a composition prepared according to the method of claim 1, the method comprising:
    fluidically coupling the first container and the second container;
    mixing an amount of preparation (a) from the first container and an amount of preparation (b) from the second container to form a mixture; and
    immediately spraying the mixture on an area of skin after the step of mixing; and
    neutralizing or inactivating any one or a combination of the following chemicals: nitric acid 65%; sulfuric acid 95%; hydrofluoric acid 40%; hydrochloric acid, smoking 36%; Sodium hypochlorite solution 10% active chlorine; hydrogen peroxide 30%; Peracetic acid 24%; ammonia 25%; caustic soda 32%; Calcium hypochlorite 76% active chlorine; Lithium hypochlorite 26% active chlorine; Formaldehyde 35%; or triacetone peroxide.

* * * * *